United States Patent [19]

Cannon et al.

[11] Patent Number: 5,258,384
[45] Date of Patent: Nov. 2, 1993

[54] S-11-HYDROXY-10-METHYLAPORPHINE AND ITS BIOLOGICALLY ACTIVE SALT FORMS AS 5HT$_{1A}$ INHIBITORS

[75] Inventors: Joseph G. Cannon, Iowa City, Iowa; Scott T. Moe, St. Paul, Minn.; John P. Long; Ranbir K. Bhatnagar, both of Iowa City, Iowa

[73] Assignee: British Technology Group Limited, London, England

[21] Appl. No.: 7,812

[22] Filed: Jan. 22, 1993

Related U.S. Application Data

[63] Continuation of Ser. No. 918,889, Jul. 24, 1992, abandoned, Continuation of Ser. No. 640,241, Jan. 11, 1991, abandoned.

[51] Int. Cl.$^5$ .................. C07D 221/18; A61K 31/47
[52] U.S. Cl. ..................................... 514/284; 546/75
[58] Field of Search ............... 514/284; 546/75

[56] References Cited

U.S. PATENT DOCUMENTS 3,717,643 2/1973 Archer ................................. 546/75
4,353,912 10/1982 Neumeyer ........................... 546/75

OTHER PUBLICATIONS

Cannon et al., "(R)-(−)-10-Methyl-11-hydroxyaporphone: A High Selective Serotonergic Agonist", *Journal of Medicinal Chemistry*, (1988), 31, 313.
Cannon et al., "5-HT$_{1A}$-Receptor Antagonism: N-Alkyl Derivatives of (R)-(−)-8,11-Dimethoxynoraporphine" *Journal of Medicinal Chemistry*, (1989), 32 1959.
Gao, et al., "Synthesis and Dopamine Agonist and Antagonist Effects of (R)-(−)- and (S)-(+)-11-Hydroxy-N-n-propylnoraporphine", *Journal of Medicinal Chemistry*, (1988), vol. 31, No. 7 1392-96.
Wikstrom et al., *Annual Reports in Medicinal Chemistry*, vol. 25, Chapter 25 (1990) 41-50.
Baldessarini, R. J. et al "Effects of isomers of hydroxyaporphines . . . " Biochem. Pharmacol., Great Britain, vol. 40 No. 3 (1990), pp. 417-423.
Park, K. H. et al "Frequency selective compounds . . . " The Jour. of Pharmacol. & Expertl. Therapeutics, vol. 255 No. 1 USA (1990), pp. 240-247.
Schaus, J. M. et al "Aporphines as antagonists of dopamine . . . " J. Med. Chem., vol. 33 No. 2 (1990), pp. 600-607.
Cunningham et al "The Interaction of Cocaine with Serotonin . . . " Neuropsychopharmacology (1990), vol. 3, No. 1, pp. 41-50.
Hutson et al "Evidence that the hyperphagic response . . . " European Journal of Pharmacology, 150 (1988), pp. 361-366.
Kennett et al "Single Administration of 5-HT$_{1a}$ agonists . . . " European Journal of Pharmacology, 138 (1987), pp. 53-60.
Stenlake, J. "Stereochemical Factors" Foundation of Molecular Pharmacology, vol. 2 London: The Athlone Press, (1979), p. 130.
Duhault et al "Brain Serotonergic System and Anorectic Drugs" Central Mechanisms of Anorectic Drugs, Raven Press, New York (1978), pp. 205-215.

*Primary Examiner*—Mukund J. Shah
*Assistant Examiner*—Philip I. Datlow
*Attorney, Agent, or Firm*—Nixon & Vanderhye

[57] ABSTRACT

S-11-hydroxy-10-methylaporphine and its biologically active salt forms are used as 5-HT$_{1A}$ inhibitors. Since these compounds function as 5-HT$_{1A}$ they can be used as an antidote for effects of cocaine and as appetite suppressants.

S-11 Hydroxy-10-Methylaporphine has the formula:

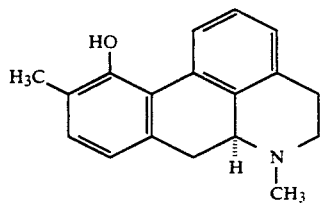

15 Claims, No Drawings

S-11-HYDROXY-10-METHYLAPORPHINE AND ITS BIOLOGICALLY ACTIVE SALT FORMS AS 5HT$_{1A}$ INHIBITORS

GRANT REFERENCE

This invention was made with government support under contract number HL38136-03 awarded by the National Institute of Health of the Department of Health and Human Services. The Government has certain rights in the invention.

This is a continuation of application Ser. No. 07/918,889, filed 24 Jul. 1992, now abandoned, which is continuation of application Ser. No. 07/640,241, filed 11 Jan. 1991, now abandoned.

BACKGROUND OF THE INVENTION

There are numerous 5-HT$_{1A}$ receptor inhibitors that are known. However, none that are currently known are selective. In other words, those that are known are often also blockers for other receptors such as dopamine, norepinephrine, and/or acetyl choline. None that are presently known are selective only for serotonin 5-HT$_{1A}$ receptor blocking.

Of course, it is highly desirable to have compounds which function very specifically for blocking of serotonin receptors since that would allow highly specific effects, without causing undesirable side effects.

Some of the potential uses that may exist for a highly specific serotonin 5-HT$_{1A}$ receptor blocker would include potential use as an antidote for counteracting the effects of cocaine and for an effective appetite suppressant.

An earlier paper by some of the present inventors has reported that R-11-hydroxy-10-methylaporphine is in fact an agonist for 5-HT$_{1A}$ receptors. It is highly surprising that the (S)-enantiomer shows no agonist effect, but in fact blocks the action of serotonin 5-HT$_{1A}$ receptors. This is a rare example of enantiomers which demonstrate exactly opposite pharmacological effects at the same receptor.

A primary objective of the present invention is to make S-11-hydroxy-10-methylaporphine and its biologically active salt forms.

Another objective of the present invention is to develop a method of selective inhibition of serotonin 5-HT$_{1A}$ receptors in mammals by administering S-11-hydroxy-10-methylaporphine or a biologically acceptable salt form thereof.

Another objective of the present invention is to provide compositions containing S-11-hydroxy-10-methylaporphine or a biologically acceptable salt form thereof which can be effectively used for an antidote for the effects of cocaine and/or for use as an appetite suppressant.

The method of accomplishing these as well as other objectives of the present invention will become apparent from the detailed description of the invention which will follow hereinafter.

SUMMARY OF THE INVENTION

A new compound in isolatable form S-11-hydroxy-10-methylaporphine and its biological active salt forms is prepared. The compound is used in a method to inhibit 5-HT$_{1A}$ neuroreceptors. This method can be useful for two purposes, namely as an antidote for the effects of cocaine and for appetite suppression. The compound is highly useful in that it is a selective serotonin 5-HT$_{1A}$ neuroreceptor inhibitor, but does not inhibit at different neurotransmitter receptors such as dopamine and acetyl choline.

DETAILED DESCRIPTION OF THE INVENTION

As earlier stated, an earlier paper of Cannon et al., *Journal of Medicinal Chemistry*, 31, 313–318 (1988) describes the pharmacological actions of the mirror image isomer of the present compound. In fact, in this paper the mirror image compound (R)-11-hydroxy-10-methylaporphine is described as an agonist for serotonin 5-HT$_{1A}$. In other words, the mirror image (R)- of the compound now isolated for the first time, not as a racemic mixture but only in the S-form, functions in the exact opposite manner, i.e. a serotonergic agonist.

S-11-hydroxy-10-methylaporphine can be illustrated by the following graphic formula:

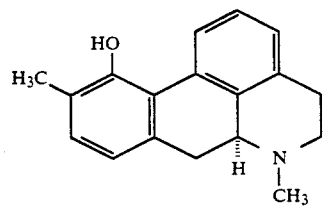

It is the S-isomer which is the active form. Typically, it is provided in a pharmaceutically acceptable salt form such as the hydrochloride salt.

As used here, pharmaceutically acceptable salt form thereof, means the following. Acceptable for use in the pharmaceutical or ceptable. "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the therapeutically active S-11-hydroxy-10-methylaporphine to achieve physiological results of the present invention can be via any of the accepted modes of administration for systemically active substances. These methods include oral, parenteral, (subcutaneous, intramolecular, intravenous), rectally, aerosol, and any otherwise systemic means of administration.

The compositions of the present invention may be any of those known in the pharmaceutical arts which are suitable for the method of administration and dosage required in any particular circumstance. Such compositions may include tablets, pills, capsules, powders, parenterals, and oral liquids including oil aqueous suspensions, solutions and emulsions, and forms for rectal administration. It may even include long acting injectables and sustained release devices.

When the dosage is in solid form, solid pharmaceutical carriers such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of S-11-hydroxy-10-methylaporphine, advisably as a nontoxic acid addition salt, and may be administered one or more at a time at regular intervals. Such unit dosage forms, however, should with a broad range guideline contain a concentration of from about 1.0 to about 25.0 mg/kg of body weight, preferably from 5.0 to 20.0 mg/kg.

A typical tablet for the specified uses mentioned herein may have the composition:

|  | Mg. |
|---|---|
| 1. S-11-hydroxy-10-methylaporphine | 1–25 |
| 2. Mannitol | 100 |
| 3. Stearic acid | 3 |

A granulation is made from the mannitol. The other ingredients are added to the dry granulation and then the tablets are punched.

Another tablet may have the composition:

|  | Mg. |
|---|---|
| 1. S-11-hydroxy-10-methylaporphine | 1–25 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with a 4 and 5, and tableted.

Capsules may be prepared by filling No. 3 hard gelatin capsules with the following ingredients, thoroughly mixed:

|  | Mg. |
|---|---|
| 1. S-11-hydroxy-10-methylaporphine | 1–25 |
| 2. Lactose U.S.P. | 200 |
| 3. Starch U.S.P. | 16 |
| 4. Talc U.S.P. | 8 |

The method of synthesis of the S-11-hydroxy-10-methylaporphine enantiomer represents a modification of the previously published preparation of the R-enantiomer, Cannon et al. *Journal of Medicinal Chemistry*, 31, 313–318, 1988.

Generally, the scheme of preparation of S-11-hydroxy-10-methylaporphine can be represented by the following schematic. The following examples are offered to further illustrate but not limit the synthesis of the S-enantiomer and its ability to bind to 5-HT$_{1A}$ receptors and to act as an antagonist to 5-HT$_{1A}$ receptors.

Scheme 1. Synthesis of (S)-(+)-11-Hydroxy-10-methylaporphine

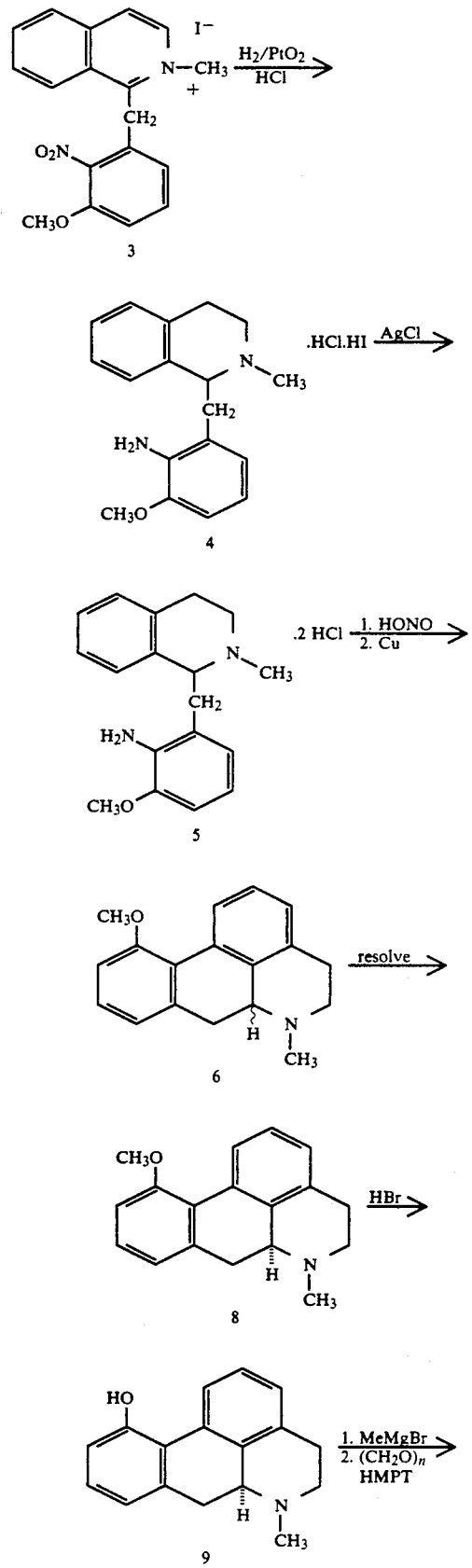

-continued
Scheme 1. Synthesis of (S)-(+)-11-Hydroxy-10-methylaporphine

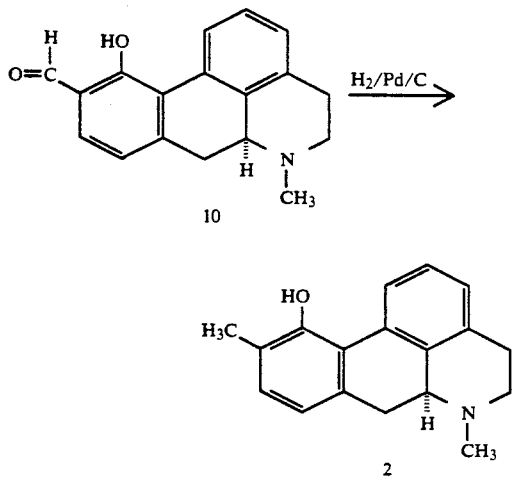

EXAMPLES

1-(2-Amino-3-methoxybenzyl)-2-methyl-1,2,3,4-tetrahydroisoquinoline Hydrochloride Hydriodide (4)

1-(3-Methoxy-2-nitrobenzyl)isoquinoline methiodide (12.7 g, 0.029 mol) in 325 mL of MeOH, 100 mL of EtOH, and 2 mL of CHCl$_3$ was hydrogenated in a Parr apparatus at 25° C. over 0.50 g of PtO$_2$ for 48 h at an initial pressure of 60 psig. Excess HCl was then bubbled through the hydrogenation mixture and it was filtered through Celite. Volatiles were removed from the filtrate under reduced pressure to give 12.4 g (96%) of an orange semi-solid. This material was used in the next step without purification. For elemental analysis, a portion was crystallized twice from MeOH-EtOAc (2:3) to give the pure HCl-HI salt, mp 210°–212° C. MS m/e 283 (M+ - HCl - HI). Anal. Calcd for C$_{18}$H$_{24}$ClIN$_2$O: C, 47.64; H, 5.50; N 6.17. Found: C, 47.42; H, 5.56; N, 6.09 (Karl Fischer H$_2$O 1.54%).

1-(2-Amino-3-methoxybenzyl)-2-methyl-1,2,3,4-tetrahydroisoquinoline Dihydrochloride (5)

A mixture of 12.2 g (0.0273 mol) of 4 and 5.0 g (0.0349 mol) of AgCl in 250 mL of MeOH was shaken on a mechanical shaker for 18 h. The Ag salts were removed by filtration through Celite and the filtrate was evaporated under reduced pressure. The solid residue was dissolved in 50 mL of MeOH-2-PrOH (4:1) and the di-HCl salt was precipitated by addition of 400 mL of EtOAc. The solid was collected on a filter and dried under N$_2$ to yield 9.5 g (98%) of product, mp 212-215C. Spectral (NMR, MS) data on this salt were identical with those obtained with the HCl-HI salt H. This material was used in the next step without purification.

(R,S)-11-Methoxyaporphine Hydrochloride (6)

Compound 5 (5.85 g, 0.065 mol) in 500 mL of 10% H$_2$SO$_4$ was cooled to −5° C. in an ice-salt bath. A solution of 1.50 g (0.0217 mol) of NaNO$_2$ in 25 mL of cold H$_2$O was added dropwise over 5 min to the rapidly stirred solution. The reaction mixture was stirred at −5° C. for 15 min, and then 2.0 g (0.315 g-atom) of freshly prepared Cu (vide infra) was added in one portion. The ice-salt bath was replaced with an ice-H$_2$O bath and the reaction mixture was stirred for 18 h (allowing the ice to melt). The resulting mixture was passed through a fritted glass filter; the filtrate was made basic with conc NH$_4$OH, and was extracted with five 100 mL portions of CHCl$_3$. The pooled extracts were dried (Na$_2$SO$_4$) and volatiles were removed under reduced pressure. The resulting dark orange oil was dissolved in 20 mL of 2-PrOH; excess ethereal HCl was added, followed by 600 mL of anhydrous Et$_2$O, to afford 3.7 g (74%) of a light orange solid, mp 215°–220° C. For elemental analysis, a small portion of this material was recrystallized twice from EtOH-Et$_2$O to give a white solid, mp 258°–261° C. (decomp). Lit[11] mp 249°–251° C. (decomp). MS m/e 266 (M+ - HCl). Anal. Calcd for C$_{18}$H$_{20}$ClNO: C, 71.63; H, 6.68; N, 4.64. Found: C, 71.46; H, 6.69; N, 4.65.

Copper for Pschorr Cyclization

A variation of a procedure of Gatterman, Untersuchungen uber Diazoverbindungen. Ber. Deutsch. Chem. Ges. 23: 1218–1228, 1890, was used. Zn dust (6.0 g, 0.092 g - atom, washed with two 50 mL portions of HCl followed by two 50 mL portions of H$_2$O) was added in 10 portions over 45 min to a rapidly stirred solution of 20.0 g (0.0125 mol) of CuSO$_4$.5H$_2$O in 100 mL of H$_2$O, at such a rate as to maintain the temperature at 20°–25° C. The mixture was stirred for 1 h more, then the aqueous layer was decanted and the solid was stirred for 1 h with 100 mL of 5% HCl. The copper was then washed with H$_2$O until the washings were neutral to pH paper.

(R)-11-Methoxyaporphine Hydrochloride (7)

To a refluxing solution of 0.95 g (0.0036 mol) of 6 in 10 mL of EtOAc was added a solution of 1.46 g (0.0036 mol) of (−)-di-p-toluoyl-L-tartaric acid (Aldrich Chemical Co.) in 15 mL of EtOAc. The mixture was heated under reflux for 1 h, then it was cooled and filtered, and the solid on the filter was washed with two 10 mL portion of EtOAc. This material was recrystallized four times from EtOAc-EtOH (1:4), to constant optical rotation. The resulting material was dissolved in 25 mL of CHCl$_3$, 25 mL of H$_2$O, and 1 mL of EtOH. The solution was made basic with 25 mL of saturated NaHCO$_3$ and the aqueous solution was extracted with three 25 mL portions of CHCl$_3$. The pooled organic extracts were dried (Na$_2$SO$_4$) and the volatiles were removed under reduced pressure. The residue was treated with ethereal HCl to produce 0.097 g (10%) of a white solid, mp 253°–255° C. (decomp). Lit[11] mp 249°–251° C. (decomp). [α]$_D^{25}$ −92.6° (c 0.606, MeOH), [α]578$^{25}$ −94.2°. Lit[1] [α]578$^{26.7}$ −85.2°. NMR and MS data for this product were identical with those of the racemic modification 6.

(S)-11-Methoxyaporphine Hydrochloride (8)

Compound 6 (1.9 g, 0.0072 mol) in 15 mL of EtOAc was treated with 1.48 g (3.66 mmol) of (+)-di-p-toluoyl-D-tartaric acid in 15 mL of EtOAc as described for 7, to afford 0.29 g (13%) of white crystals, mp 257°–259° C. (decomp). [α]$_D^{25}$ +94.3° (c 0.51, MeOH), [α]578$^{25}$ +98.3° (c 0.51, MeOH). NMR and MS data for this product were identical with those of the (RS) modification 6 and of the (R)-enantiomer 7.

(S)-11-Hydroxyaporphine Hydrochloride (9)

A solution of 0.300 g (1.13 mmol) of 8 in 10 mL of 48% HBr was heated at 125° C. for 4 h. The cooled reaction mixture was filtered and the solid on the filter was washed with two 5 mL portions of Me$_2$CO-Et$_w$O (3:1) to give a white solid, $[\alpha]D^{25}+64.7°$ (C 0.49, MeOH), $[\alpha]578^{25}+69.7°$ (c 0.49, MeOH). This material was treated with sat NaH-CO$_3$ and the aqueous solution was extracted with three 50 mL portions of CHCl$_3$. The pooled extracts were dried (Na$_2$SO$_4$) and volatiles were taken to dryness under reduced pressure to produce a 0.228 g (91%) of the free base ($[\alpha]D^{25}+115°$ (c 0.51, MeOH); $[\alpha]578^{25}+115^{25}$ (c 0.51, MeOH). A portion of this material was converted into the HCl salt with ethereal HCl, and this was crystallized from EtOH-MeOH-Et$_2$O to produce a white solid, mp 179°-181° C. (decomp). $[\alpha]D^{25}+75.4°$ (c 0.45, MeOH) and $[\alpha]578^{25}+73.2°$ (c 0.45, MeOH). Lit[1] value for (R) enantiomer $[\alpha]578^{25}-71.2°$ (c 0.52, MeOH). NMR and MS data for this material were identical with those of the racemic modification.

(S)-10-Formyl-11-hydroxyaporphine Hydrochloride (10)

This reaction was performed in a dry box under N$_2$ (10% relative humidity). A suspension of 0.228 g (0.908 mmol) of 9 in 10 mL of benzene was added in 0.5 mL portions over 20 min to a solution of 0.45 mL (1.36 mmol) of MeMgBr (3.0M in Et$_2$O) in 10 mL of benzene. The mixture was stirred at room temperature for 30 min. A solution of 0.243 g (1.36 mmol) of hexamethylphosphorous triamide in 1 mL of benzene was added. The mixture was stirred for 15 min, then a suspension of 0.273 g (9.08 mmol) of paraformaldehyde in 2 mL of benzene was added. The mixture was heated under reflux for 4 h, cooled, and transferred to a 1 L beaker. Two hundred milliliters of 5% HCl was added and the resulting mixture was stirred for 10 min. The mixture was made basic with solid NaHCO$_3$ and was extracted with 100 mL of Et$_2$O, then with four 75 mL portions of CHCl$_3$. The combined extracts were dried (Na$_2$SO$_4$) and volatiles were removed under reduced pressure to produce a green oil which was converted into its HCl salt with ethereal HCl. The salt was washed with two 5 mL portions of abs EtOH to give 0.130 g (46%) of a white solid, mp 255°-258° C. (decomp). Lit[1] mp of (R) enantiomer 260°-262° C. (decomp).

(S)-11-Hydroxy-10-methylaporphine Hydrochloride (2)

A solution of 0.120 g (0.429 mmol) of 10 in 50 mL of MeOH-CHCl$_3$ (1:1) was hydrogenated at 50° C. for 48 h over 0.050 g of 10% Pd/C at an initial pressure of 50 psig. The cooled reaction mixture was filtered through Celite and the filtrate was evaporated under reduced pressure. The residue was treated with Et$_2$O to produce a white precipitate which was recrystallized from EtOH-Et$_2$O to provide 0.056 g (43%) of a white solid, mp 268°-270° C. (decomp). Lit[1] mp of (R) enantiomer 270°-272° C. (decomp). $[\alpha]D^{25}+101$ (c 0.54, MeOH), $[\alpha]578^{25}+104°$ (c 0.54, MeOH). Lit[1] value for (R) enantiomer $[\alpha]578^{26.7}-85.2°$ (c 0.55, MeOH).

Pharmacological activity of the active compound of the present invention and its ability to bind were next studied. Binding studies to determine the affinity of both the R (compound 1) and S (compound 2) for 5-HT$_{1A}$ sites were conducted as previously described. Rat cortex was homogenized in ice cold solution, centrifuged to isolate the membranes, and then washed. The final assay mixture included 50 mM Tris buffer (pH 7.5), 5% (w/v) homogenized rat cortex, 10 uM pargyline, 0.1% ascorbic acid, 4 mM CaCl$_2$, 1 nM [$^3$H]8-OH DPAT, and appropriate concentrations of compound 1 or compound 2. Nonspecific binding was defined as binding remaining in the presence of 10 uM of 5-HT. $K_i$ values were determined by weighted nonlinear least square curve fitting with a LIGAND program using a KD value for [$^3$H]8-OH-DPAT of 1.9 nM obtained from saturation curves.

Studies Using Guinea Pig Ilea

Guinea pigs were anesthetized with 35 mg of pentobarbital Na, administered i.p. Two centimeters of ileum, 10 cm from the cecum; was placed in Krebs-Ringer solution, and longitudinal muscle contractions were measured using a Stateham GT-03 force transducer. Contractions were recorded using a Beckman R-611 recorder. The contractions were induced using transmural single shock stimulation (0.1 Hz), and were inhibited by 10$^{-8}$M atropine sulfate, After stabilization of the contractions, compounds 1 and 2 were tested either for their ability to inhibit contractions or for their ability to antagonize the inhibitory action of 8-OH DPAT. 5-HT$_{1A}$ receptor agonists can inhibit muscle contractions by approximately 35% in this preparation.

Melting points were determined in open glass capillaries with a Melt-temp apparatus, and are uncorrected. Mass spectra were obtained with a Ribermag R10-10C mass spectrometer. Nuclear magnetic resonance spectra were recorded on Brucker-IBM NR-80 MHz and NR-360 MHz spectrometers; chemical shifts are reported downfield from internal Me$_4$Si ( scale). Elemental analyses were performed by Galbraith Laboratories, Knoxville, Tenn. Optical rotations were obtained with a Perkin-Elmer Model 141 digital polarimeter. Flash chromatography and vacuum flash chromatography were performed using Analtech 150A, 35-75 u silica gel. Spinning thin layer chromatography was performed on a Chromatotron apparatus (Harrison Research) using Kieselgel 60 PF254 (EM Science) as the stationary phase. All reactions were conducted under N$_2$ unless otherwise stated.

Table 1 shows the similarity for compounds 1 and 2 in the binding studies and their opposite activity using guinea pig ilea.

TABLE 1

| | | Biological Properties of Enantiomers of 11-Hydroxy-10-methylaporphine | | |
|---|---|---|---|---|
| Compd. no. | Absolute Configuration | Radioligand Binding Constant vs. 8-OH-DPAT $K_i$ (nM) | Ed$_{50}$ ($\mu$M) for Antagonism of inhibiting of contraction by 8-OH-DPAT[a] | Single Shock Stimulation of Guinea Pig Ileum ED$_{50}$ ($\mu$M) for inhibition of contractions |
| 1 | R | 3.1 | inactive | 0.05 (0.01–0.1) |
| 2 | S | 39.0 | 0.03 (0.01–0.08) | inactive |

[a]Concentration of 8-OH-DPAT used was 0.06 $\mu$M. This concentration produced maximal inhibition of contractions induced by transmural stimulation and were approximately 35%.

Both enantiomers are potent in their ability to displace [$^3$H] 8-hydroxy-2-di-n-propylaminotetralin ("8-OH DPA") from membranes of rat forebrain. Unfortunately, this experimental procedure does not indicate whether a chemical is an agonist or an antagonist at the binding sites for 8-OH DPAT. In all probability the binding sites are 5-HT$_{1A}$; however, it has recently been shown that 8-OH DPA also interacts with [α] receptors within the CNS. Functional studies using guinea pig ilea (Table 1) demonstrate clearly the opposing actions of 1 and 2. the (R)-enantiomer 1 is a potent inhibitor of contractions induced by single shock stimulation of cholinergic neurons, and this inhibition is antagonized by the (S)-enantiomer 2. The (S)-enantiomer 2 also antagonized inhibition induced by 8-OH DPAT, but it did not facilitate nor inhibit contractions induced by field stimulations. The above results were also obtained in the presence of $10^{-6}$M prazosin, so there is no evidence for involvement of a$_1$ adrenoceptors in the responses described above.

Two or three washings following inhibition of contractions by 1 or 8-OH DPAT returned responses to induced electrical stimulation to control levels. The (S)-enantiomer 2 was difficult to remove from the preparation and repeated washings over 2-3 hours were required to reestablish the sensitivity of the preparation to 1 or to 8-OH DPAT. The (S)- enantiomer 2 (1 um) did not alter the resting tone of the ileum, nor did it alter response to electrical stimulation. Compound 2 (1 uM) did not alter the ileum stimulating properties of potassium chloride or of nicotine. Thus, there is no evidence that 2 is acting as a smooth muscle depressant.

The phenomenon of opposite pharmacological effects (agonism-antagonism) exhibited by enantiomers has been demonstrated in this instance to be produced by derivatives of the same ring system, the aporphine, at two different neurotransmitter receptors (dopamine serotonin). This is unexpected. Moreover, since serotonin 5-HT$_{1A}$ inhibition is known to be effective in counteracting the effects of cocaine and to be involved with appetite suppression, use of the S-11-hydroxy-10-methylaporphine or its biologically active salt forms for these purposes is indicated by the pharmacological data presented herein. It can therefore be seen that the invention accomplishes at least all of its stated objectives.

What is claimed is:

1. S-11-hydroxy-10-methylaporphine and its biologically active salt forms.
2. The compound of claim 1 wherein the salt form is the hydrogen chloride.
3. A method of inhibiting 5-HT$_{1A}$ neuroreceptors in mammals, said method comprising:
   administering to the mammal a small but 5-HT$_{1A}$ inhibiting effective amount of the compound S-11-hydroxy-10-methylaporphine or a biologically acceptable salt form thereof.
4. The method of claim 3 wherein the administration is by injection.
5. The method of claim 3 wherein the administration is by oral dosage.
6. The method of claim 3 wherein the dose level is from about 1.0 mg/kg of body weight to about 25.0 mg/kg of body weight.
7. The method of claim 6 wherein the dose level is from 5.0 mg/kg of body weight to about 20.0 mg/kg of body weight.
8. The method of claim 3 wherein 5-HT$_{1A}$ neuroreceptor inhibition is used for an antidote for cocaine.
9. The method of claim 3 wherein 5-HT$_{1A}$ neuroreceptor inhibition is used for appetite suppression.
10. A composition useful for selectively inhibiting 5-HT$_{1A}$ receptor neurotransmission, comprising:
    a small but 5-HT$_{1A}$ receptor effective amount of the compound S-11-hydroxy-10-methylaporphine or a biologically acceptable salt form thereof and a suitable physiologically acceptable carrier therefore.
11. The composition of claim 10 which is in the form of an injectible.
12. The composition of claim 10 which is in the form of an oral dose.
13. The composition of claim 12 wherein the oral dose is a liquid.
14. The composition of claim 12 wherein the oral dose is a pill.
15. The composition of claim 10 wherein the amount of S-11-hydroxy-10-methylaphorphine is sufficient to dose at least 5.0 mg/kg of body weight on a unit dose basis.

* * * * *